United States Patent [19]
Stauffer

[11] Patent Number: 5,097,083
[45] Date of Patent: * Mar. 17, 1992

[54] PROCESS FOR THE CHLORINATION OF ETHANE

[76] Inventor: John E. Stauffer, 6 Pecksland Rd., Greenwich, Conn. 06831

[*] Notice: The portion of the term of this patent subsequent to Feb. 6, 2007 has been disclaimed.

[21] Appl. No.: 297,087

[22] Filed: Jan. 13, 1989

Related U.S. Application Data

[63] Continuation-in-part of Ser. No. 40,838, Apr. 20, 1987, abandoned, which is a continuation-in-part of Ser. No. 842,189, Mar. 21, 1986, abandoned.

[51] Int. Cl.$^5$ .................. C07C 17/10; C07C 17/158
[52] U.S. Cl. .................. 570/241; 570/224; 570/244; 570/261
[58] Field of Search .............. 570/241, 261, 224

[56] References Cited

U.S. PATENT DOCUMENTS

| | | | |
|---|---|---|---|
| 2,447,410 | 8/1948 | Hampel | 570/220 |
| 2,547,139 | 4/1951 | Randall | 260/660 |
| 3,420,901 | 1/1969 | Schulz | 570/243 |
| 3,642,918 | 2/1972 | Bohl et al. | 570/224 |
| 4,192,822 | 3/1980 | Sweeney et al. | 570/261 |
| 4,899,000 | 2/1990 | Stauffer | 570/222 |
| 4,990,696 | 2/1991 | Stauffer | 568/893 |

OTHER PUBLICATIONS

Stauffer, application Ser. No. 07/297,298.

Primary Examiner—J. E. Evans
Attorney, Agent, or Firm—Krass & Young

[57] ABSTRACT

A process is provided for the chlorination of ethane using hydrogen chloride, chlorine or mixtures as the chlorinating agent. The process includes reaction steps operated in tandem in separate zones first comprising the reaction of perchloroethylene with hydrogen chloride and oxygen in the presence of an oxychlorination catalyst to give hexachloroethane and water, and second comprising the vapor phase reaction of hexachloroethane with ethane feedstock to produce chlorinated ethanes, chlorinated ethylenes, and hydrogen chloride.

8 Claims, 1 Drawing Sheet

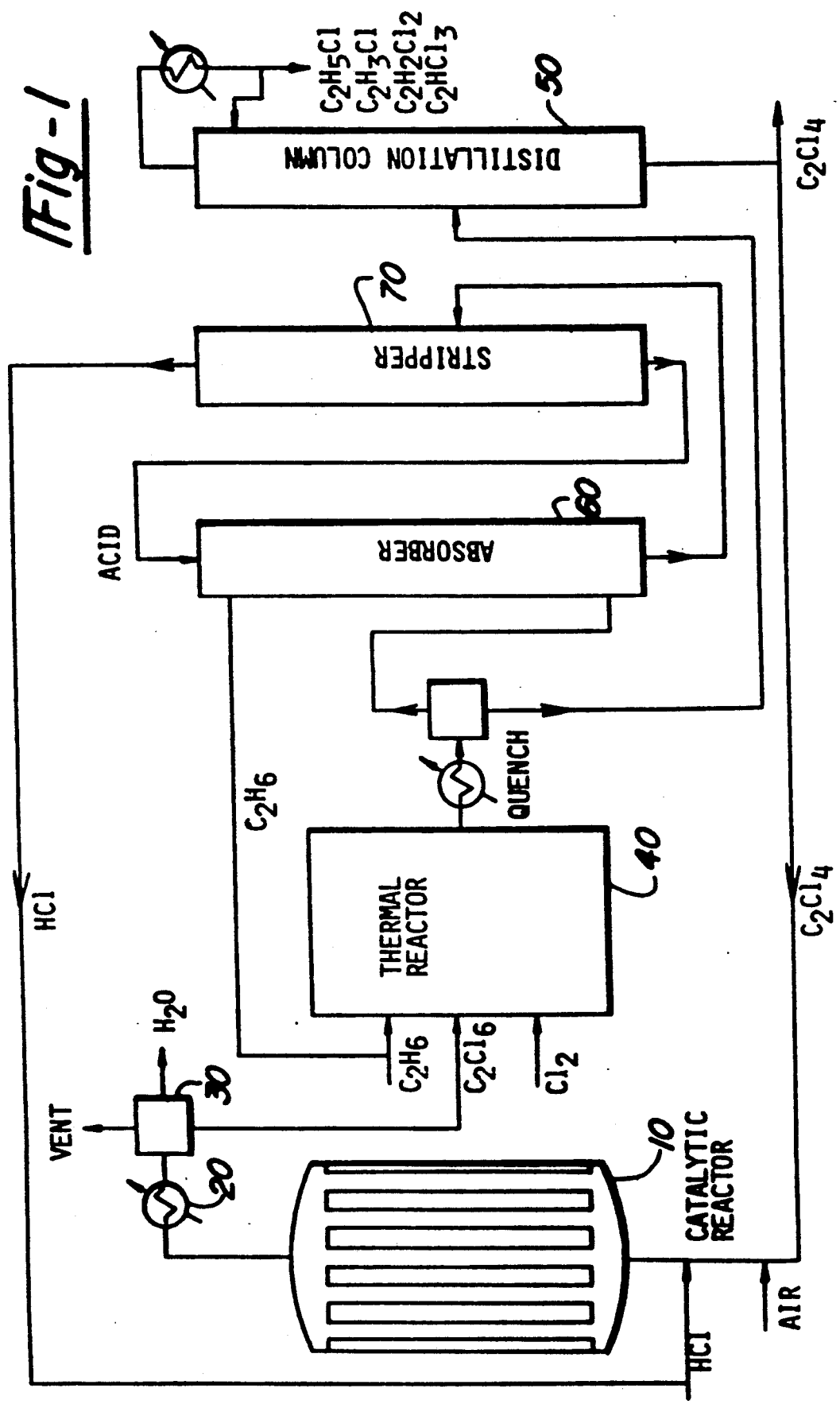

PROCESS FOR THE CHLORINATION OF ETHANE

REFERENCE TO A RELATED APPLICATION

This application is a continuation-in-part of copending application Ser. No. 040,838 filed Apr. 20, 1987, now abandoned, which in turn is a continuation-in-part of copending application Ser. No. 842,189 filed Mar. 21, 1986, now abandoned.

FIELD OF THE INVENTION

This invention relates to a novel method of chlorinating ethane using hydrogen chloride, chlorine, or any proportion of these two reagents $HCl/Cl_2$ as the chlorinating agent. The principal products are ethyl chloride ($C_2H_5Cl$) and unsaturated chlorinated hydrocarbons with two carbon atoms. The latter include vinyl chloride ($CH_2=CHCl$), vinylidene chloride ($CH_2=CCl_2$), trichlorethylene ($CHCl=CCl_2$), and perchloroethylene ($CCl_2=CCl_2$) By adjusting the process conditions, the output of vinyl chloride can maximized.

BACKGROUND OF THE INVENTION

Description of the Prior Art

The foregoing products have traditionally been prepared from more expensive sources of hydrocarbons. Dating back to the early part of this century, the large scale production of vinyl chloride, trichloroethylene and perchloroethylene commenced with the use of acetylene. Produces from calcium carbide, which consumes large quantities of electric energy, acetylene remained a relatively expensive raw material. When the ethylene oxychlorination process was developed during the 1950's, acetylene was supplanted by less costly ethylene as a feedstock for chlorinated hydrocarbons. Up to the present time practically all chlorinated ethane/ethylene products have been derived from ethylene.

Although ethylene is produced in large quantities by world-scale plants, its cost is necessarily higher than the price of ethane from which it is preferentially made. Contributing to ethylene's cost is the necessity of employing complex, high-temperature cracking processes with inherent inefficiencies. Therefore, there would be a significant advantage of substituting ethane for ethylene in the manufacture of chlorinated ethane/ethylene provided flexibility is not lost in using any proportion of hydrogen chloride and chlorine as the source of chlorine values. Particularly in the case of the manufacture of vinyl chloride, which requires about 0.45 pounds of ethylene per pound of product, any savings in the cost of hydrocarbon raw material would be important.

In order to circumvent the shortcomings of existing technology, numerous attempts have been made to oxychlorinate ethane by cost-effective means. Methods, for example, employing oxyhalogenation and related technology are described in U.S. Pat. Nos. 3,470,260, 2,334,033, 2,498,546, 3,173,962, 3,345,422, 4,000,205, 4,020,117, 4,284,833, 4,375,569, 4,386,228, 4,446,249, 4,461,919, and 4,467,127.

It is therefore an object of the present invention to provide a method for the chlorination of ethane that overcomes the disadvantages of the conventional methods.

It is also an object to provide a method of the kind described which includes endothermic and exothermic reactions, namely substitution chlorination and dissociation, that are carried out in tandem such that the overall energy requirements can be closely balanced.

These and other objects, features and advantages of the invention will be apparent from the following description and the accompanying drawings in which:

BRIEF DESCRIPTION OF THE DRAWING

FIG. 1 is a diagrammatic representation of preferred means for operating the present chlorination method including a shell and tube catalytic reactor in series with a thermal reactor with means for recycling and for withdrawal of chlorinated product and fractionation.

SUMMARY OF THE INVENTION

In one preferred embodiment of the present invention, two separate reaction steps are carried out in tandem. First, perchloroethylene is reacted with hydrogen chloride and air or oxygen in the presence of a catalyst to produce hexachloroethane and water. Second, the hexachloroethane is isolated from the reaction products and is reacted in the vapor phase with ethane to give predominantly the desired chlorinated hydrocarbons plus hydrogen chloride. The latter is recycled to the first reaction step so that there is no net production of hydrogen chloride.

The invention in another preferred embodiment concerns a process for the chlorination of ethane using hydrogen chloride as the source of chlorine; said process including steps operated in tandem; first, subjecting chlorinated ethylene consisting essentially of perchloroethylene to oxychlorination with hydrogen chloride and oxygen in the presence of an oxychlorination catalyst to give reaction products consisting essentially of hexachloroethane and water; second, isolating said hexachloroethane from the reaction products and reacting it with ethane feedstock in the vapor phase to produce chlorinated ethanes, chlorinated ethylenes including perchloroethylene, and hydrogen chloride and third, isolatinq said products of the second step and repeating the first step using as starting materials the perchloroethylene and hydrogen chloride thus isolated whereby chlorination is accomplished using regenerated hexachloroethane, the process is operated with total utilization of hydrogen chloride, and net production of hydrogen chloride is avoided.

The reactions of the proposed process are illustrated by the following equations for the preparation of vinyl chloride.

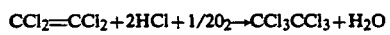

$$CCl_2=CCl_2+2HCl+1/2O_2 \rightarrow CCl_3CCl_3+H_2O$$

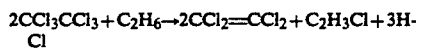

$$2CCl_3CCl_3+C_2H_6 \rightarrow 2CCl_2=CCl_2+C_2H_3Cl+3HCl$$

By balancing the above equations, one obtains the net reaction as follows:

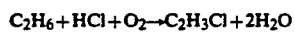

$$C_2H_6+HCl+O_2 \rightarrow C_2H_3Cl+2H_2O$$

In one preferred embodiment in which chlorine is added to the second reaction step, the following reaction occurs:

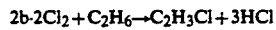

$$2b\text{-}2Cl_2+C_2H_6 \rightarrow C_2H_3Cl+3HCl$$

The first reaction step in which perchloroethylene is oxychlorinated to hexachloroethane may typically be carried out in a molten salt reactor, fluidized bed reactor, or in a shell and tube reaction in order to obtain efficient heat removal. The temperature is maintained within the range of about 200° to about 375° C. The catalyst of choice is copper chloride deposited on an inert support. This is the well-known Deacon catalyst, which has been used in experimental processes to produce chlorine from hydrogen chloride and air. In a preferred embodiment, any of various salts may be admixed with the copper chloride catalyst to promote its effectiveness, e.g., potassium chloride, ferric chloride, and lead chloride.

The second reaction step is conducted in the vapor phase at elevated temperatures, e.g., in the range from about 400° to about 700° C. The required temperature is related to the reaction time; for example, a shorter retention time can be used at higher temperatures. Should insufficient hydrogen chloride be available to produce the required hexachloroethane, supplemental chlorine can be added to the second reaction step. Thus, any proportion of hydrogen chloride and chlorine can be used in the overall process. In a preferred embodiment, partially chlorinated ethane or ethylene produced in step 2 is recycled to step 2 for further chlorination. A preferred ethane feedstock to step 2 comprises a chlorinated ethane or mixture of chlorinated ethanes.

The mechanism by which ethane is chlorinated in the second reaction step is complex, but certain rules are helpful in clarifying the chemistry. In actuality, both chlorination and dehydrochlorination occur together. Thus, the invention contemplates that ethane forms dichloroethane by substitution chlorination and this compound in turn is dehydrochlorinated to give vinyl chloride. The intermediate product ethyl chloride, because of its relative thermal stability, does not disassociate appreciably to give ethylene.

At the elevated temperature at which the second reaction step is conducted, addition chlorination across a double bond is negligible. Furthermore, substitution chlorination of unsaturated compounds is known to be slower than that for saturated compounds. Therefore, according to the invention, ethane and ethyl chloride are preferentially chlorinated instead of vinyl chloride, and the latter, once formed, is relatively stable.

In a preferred embodiment, by modifying the conditions under which the second reaction step is carried out, the proportion of products may be adjusted. Thus, preferably, by using a large excess of ethane, by recycling ethyl chloride to the reactor, and by preventing the back-mixing of vinyl chloride in the reactor, the output of vinyl chloride can be maximized. If, on the other hand, the more highly chlorinated products, such as trichloroethylene, are desired, more severe conditions can be used. Under the latter conditions, a higher proportion of hexachloroethane is supplied to the reactor, and higher vapor phase temperatures in the above range are preferred.

The temperature control of the second reaction step is facilitated by the simultaneous chlorination and dehydrochlorination reactions. This advantage was pointed out in U.S. Pat. No. 2,547,139. Substitution chlorination, e.g., the formation of ethyl chloride from ethane, is exothermic or heat producing. Dehydrochlorination such as occurs in the formation of vinyl chloride from dichloroethane is endothermic or heat absorbing. By conducting the chlorination and dehydrochlorination reactions in an intimate manner, the heat requirements can be more nearly balanced.

DETAILED DESCRIPTION OF THE PREFERRED EMBODIMENT

Referring to the drawings, FIG. 1 is a schematic view of the operation of a preferred embodiment of the process of the invention. Air, hydrogen chloride and perchloroethylene are fed to the shell and tube reactor 10 which contains the copper chloride catalyst. The oxychlorination reaction is carried out in the reactor 10, and the effluent is cooled in a condensor 20 to condense the liquids. The inert gases are vented while the water is decanted from the chlorinated organics in a separator 30. Hexachloroethane, including hexachloroethane dissolved in any unreacted perchloroethylene, is pumped to the thermal reactor 40 where in the vapor phase reaction which ensues with ethane feedstock, it serves to chlorinate the ethane.

The hot vapors from the thermal reactor 40 are preferably quenched (for example, with a stream of cold perchloroethylene) to minimize the formation of heavy ends and tars. Unreacted ethane and hydrogen chloride are separated from the chlorinated organics which as products are pumped to a distillation column 50 for fractionation. In an absorber 60, hydrogen chloride is separated from the unreacted ethane by absorption in weak hydrochloric acid and fed to a stripper 70. In a preferred embodiment, the stripped hydrogen chloride is recycled to the catalytic reactor 10. The perchloroethylene still bottoms are returned also to the catalytic reactor for the oxychlorination step. After further fractionation in another column (not shown), ethyl chloride and, if desired, other light ends may be recycled with the unreacted ethane to the thermal reactor 40. The principal products obtained by distillation are ethyl chloride, vinyl chloride, vinylidene chloride, trichloroethylene and perchloroethylene.

Although the process as described seems rather straightforward, successful operation depends on the strict adherence to the following rules:

1. Hexachloroethane produced via oxychlorination must be isolated from the reaction products before being fed to the thermal reactor. Any impurities, with the exception of perchloroethylene, must be separated from the hexachloroethane in order to avoid the formation of byproducts, which are difficult to separate and which reduce the hydrogen chloride efficiency. The thermal reactor must be kept under anhydrous conditions or above the dew point to prevent severe corrosion problems. All oxygen has to be excluded from the thermal reactor to avoid burning and to prevent the formation of water.

2. Hydrogen chloride, before being recycled to the oxychlorination reactor, must be freed of all hydrocarbons to prevent combustion reactions and to avoid pollution problems caused by the release of hydrocarbons in the vent gases.

3. Perchloroethylene that is reformed in the thermal reactor must be isolated from the product stream before being recycled to the oxychlorination reactor. Any saturated hydrocarbons which are fed to the oxychlorination reactor will be subject to burning. Unsaturated hydrocarbons, other than perchloroethylene, will be chlorinated in the oxychlorination reactor and eventually lead to unwanted byproducts. Any volatile impurities will escape in the vent gases.

The necessary separations of the recycle streams cannot be taken for granted. For example, hexachloroethane is very slightly miscible in water and thus presents a challenge in drying it completely. The principles of azeotropic distillation are used to separate hydrogen chloride. And finally, in isolating perchloroethylene from the product stream the differences in boiling points determine its ease of fractionation.

The products produced by the present invention are valuable items of commerce. Vinyl chloride monomer is consumed in huge quantities in the manufacture of plastic materials. Vinylidene chloride is another valuable monomer which is used to produce specialty films known commonly by the Saran tradename. Trichloroethylene is an effective degreasing solvent employed by the aircraft, automotive, and other metal fabricating industries. Because of its relative safety and flame retardency, perchloroethylene is a popular dry cleaning solvent for woolen garments and other clothes.

What is desired to claims as my exclusive privilege and property in the invention as described is the following.

I claim:

1. A process for the chlorination of ethane using hydrogen chloride as the source of chlorine and avoiding net production of hydrogen chloride, said process consisting essentially of steps operated in tandem;

first, subjecting chlorinated ethylene consisting essentially of perchloroethylene to oxychlorination with hydrogen chloride and oxygen in the presence of an oxychlorination catalyst to give reaction products consisting essentially of hexachloroethane and water;

second, isolating said hexachloroethane from the reaction products of the first step and reacting it with ethane feedstock in the vapor phase to produce chlorinated ethanes, chlorinated ethylenes including perchloroethylene, and hydrogen chloride;

and third, isolating perchloroethylene and hydrogen chloride from hydrocarbon products of the second step and recycling the hydrogen chloride and perchloroethylene thus isolated to the first step whereby chlorination is accomplished using regenerated hexachloroethane, the process is operated with total utilization of hydrogen chloride, and net production of hydrogen chloride is avoided.

2. A process according to claim 1 in which elemental chlorine is added to step 2.

3. A process according to claim 1 in which partially chlorinated ethane/ethylene produced in step 2 is recycled to step 2 for further chlorination.

4. A process according to claim 1 in which the ethane feedstock to step 2 comprises a chlorinated ethane or a mixture of chlorinated ethanes.

5. A process according to claim 1 in which the catalyst used in step 1 comprises copper chloride on an inert support.

6. A process according to claim 5 where the catalyst comprises an admixture of copper chloride with salt selected from the group consisting of potassium chloride, ferric chloride, and lead chloride.

7. A process according to claim 1 in which the oxychlorination reaction in step 1 is carried out at temperatures in the range of about 200° to about 375° C.

8. A process according to claim 1 in which the vapor phase ethane chlorination reaction is carried out at temperatures in the range from about 400° to about 700° C.

* * * * *